US00RE40607E

(19) United States
(12) Reissued Patent
Hsieh et al.

(10) Patent Number: US RE40,607 E
(45) Date of Reissued Patent: Dec. 16, 2008

(54) METHODS AND APPARATUS FOR SCOUT-BASED CARDIAC CALCIFICATION SCORING

(75) Inventors: Jiang Hsieh, Brookfield, WI (US); Mark Edward Woodford, Waukesha, WI (US)

(73) Assignee: General Electric Company, Schenectady, NY (US)

(21) Appl. No.: 10/613,791

(22) Filed: Jul. 3, 2003

Related U.S. Patent Documents

Reissue of:
(64) Patent No.: 6,256,368
Issued: Jul. 3, 2001
Appl. No.: 09/419,191
Filed: Oct. 15, 1999

(51) Int. Cl.
*H05G 1/62* (2006.01)
*G01N 23/083* (2006.01)

(52) U.S. Cl. ..... 378/98.12; 378/8; 378/95
(58) Field of Classification Search ..... 378/4–20, 378/95, 98.12
See application file for complete search history.

(56) References Cited

U.S. PATENT DOCUMENTS 4,433,428 A * 2/1984 Haendle et al. ..... 378/95
4,456,926 A * 6/1984 Kruger et al. ..... 378/98.12
4,677,478 A * 6/1987 Kruger et al. ..... 378/98.12
4,716,904 A * 1/1988 Meno ..... 600/431
5,583,901 A * 12/1996 Reitter et al. ..... 378/4
6,154,516 A 11/2000 Heuscher et al.
6,226,350 B1 5/2001 Hsieh
6,236,705 B1 * 5/2001 Stergiopoulos et al. ..... 378/8
6,252,924 B1 6/2001 Davantes et al.
6,256,368 B1 7/2001 Hsieh et al.
6,381,487 B1 * 4/2002 Flohr et al. ..... 600/425
6,421,552 B1 7/2002 Hsieh
6,510,337 B1 1/2003 Heuscher et al.
6,560,309 B1 5/2003 Becker et al.
6,690,965 B1 * 2/2004 Riaziat et al. ..... 600/428

* cited by examiner

*Primary Examiner*—Chih-Cheng G Kao
*Assistant Examiner*—Thomas R Artman
(74) *Attorney, Agent, or Firm*—Armstrong Teasdale LLP

(57) ABSTRACT

In one aspect, the present invention is a method for producing CT images of a patient's heart suitable for calcification scoring, in which the heart has a cardiac cycle. The method includes steps of acquiring data representative of a first scout-scanned CT image of physical locations of the patient's body including at least a portion of the patient's heart at phases $\phi_1(L)$ of the cardiac cycle, acquiring data representative of a second scout-scanned CT image of the physical locations of the patient's body including at least a portion of the patient's heart at phases $\phi_2(L)$ of the cardiac cycle different from $\phi_1(L)$ at physical positions L of interest, and determining a difference image from the acquired data representative of the first scout-scanned CT image and the acquired data representative of the second scout-scanned CT image data. It is not necessary that $\phi_1(L)$ and $\phi_2(L)$ be constant as a function of position L.

31 Claims, 5 Drawing Sheets

METHODS AND APPARATUS FOR SCOUT-BASED CARDIAC CALCIFICATION SCORING

Matter enclosed in heavy brackets [ ] appears in the original patent but forms no part of this reissue specification; matter printed in italics indicates the additions made by reissue.

BACKGROUND OF THE INVENTION

This invention relates generally to methods and apparatus for cardiac CT imaging, and more particularly to methods and apparatus that minimize an impact of heart motion in collecting calcification data from coronary images.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam interests the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

A main objective of cardiac CT applications is to perform calcification scoring, a diagnostic procedure in which an amount of calcification present in a patient's heart is estimated. At least one known CT imaging system requires about 0.5 s to complete data acquisition for an image. Although this speed is satisfactory for general imaging purposes, it is not fast enough to avoid motion-induced image artifacts in cardiac CT imaging, in which a typical cardiac cycle is about 1.0 s long. These artifacts present major problems for cardiac calcification scoring.

At least one other known CT imaging system reduces motion-induced image artifacts by acquiring data rapidly enough to effectively freeze cardiac motion. This imaging system employs a scanning electron beam to generate a moving source of x-rays rather than an x-ray source and detector on a rotating gantry. However, CT imaging systems employing scanning electron beams are quite expensive and are not available at many hospitals.

It would therefore be desirable to provide methods and apparatus that overcome motion-induced artifacts produced in images acquired by CT imaging systems having relatively slow scanning and detection systems such as rotating gantries. It would also be desirable to provide cardiac calcification scoring methods and apparatus utilizing such CT imaging systems. It would further be desirable to provide methods and apparatus that can readily identify and score calcification from the small incremental x-ray attenuation produced by small amounts of calcification.

BRIEF SUMMARY OF THE INVENTION

There is therefore provided, in one embodiment of the present invention, a method for producing CT images of a patient's heart suitable for calcification scoring, in which the heart has a cardiac cycle. The method includes steps of acquiring data representative of a first scout-scanned CT image of physical locations of the patient's body including at least a portion of the patient's heart at phases $\phi_1(L)$ of the cardiac cycle, acquiring data representative of a second scout-scanned CT image of the physical locations of the patient's body including at least a portion of the patient's heart at phases $\phi_2(L)$ of the cardiac cycle different from $\phi_1(L)$ at physical positions L of interest, and determining a difference image from the acquired data representative of the first scout-scanned CT image and the acquired data representative of the second scout-scanned CT image data. It is not necessary that $\phi_1(L)$ and $\phi_2(L)$ be constant as a function of position L.

The above described embodiment overcomes motion-induced image artifacts by making calcification signals more readily observable as a change between images. Moreover, even small amounts of calcification are readily identifiable and qualifiable, because much larger variations in x-ray attenuations that would otherwise hide calcification deposits are canceled out.

BRIEF DESCRIPTION OF THE DRAWINGS

FIGS. 6, 7, and 8 should not necessarily be assumed to be drawn to the same scale.

DETAILED DESCRIPTION OF THE INVENTION

Figure 1:
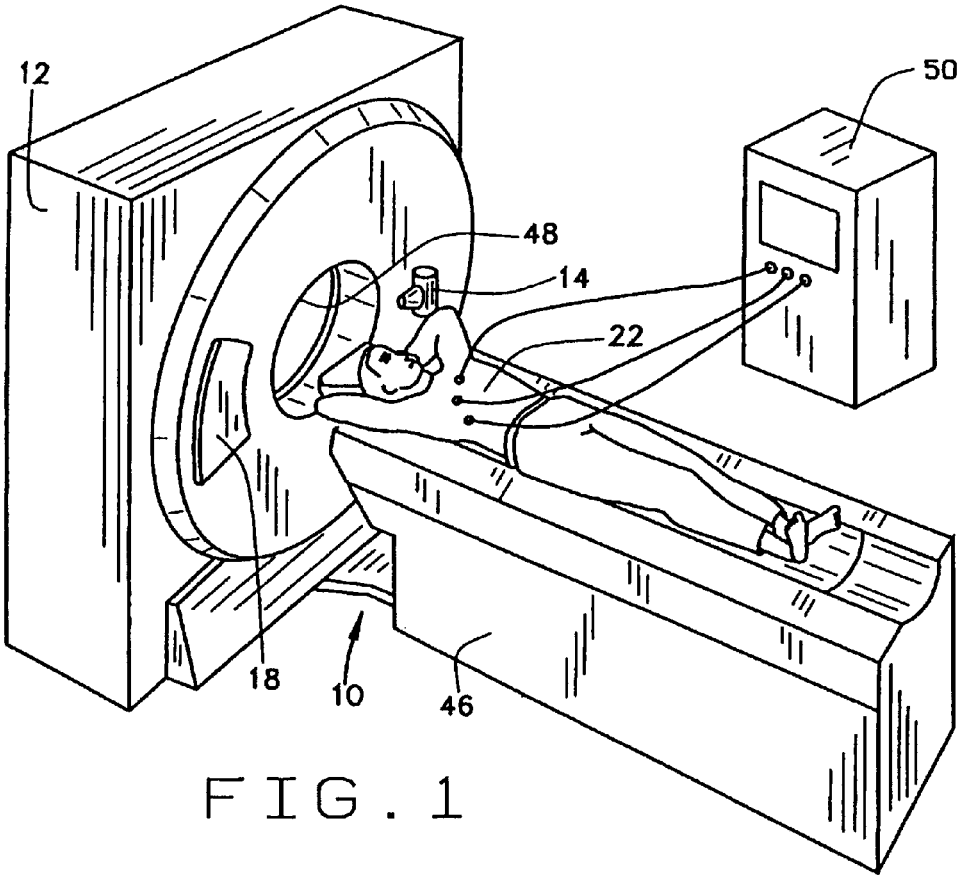
FIG. 1 is a pictorial view of a CT imaging system.
Figure 2:
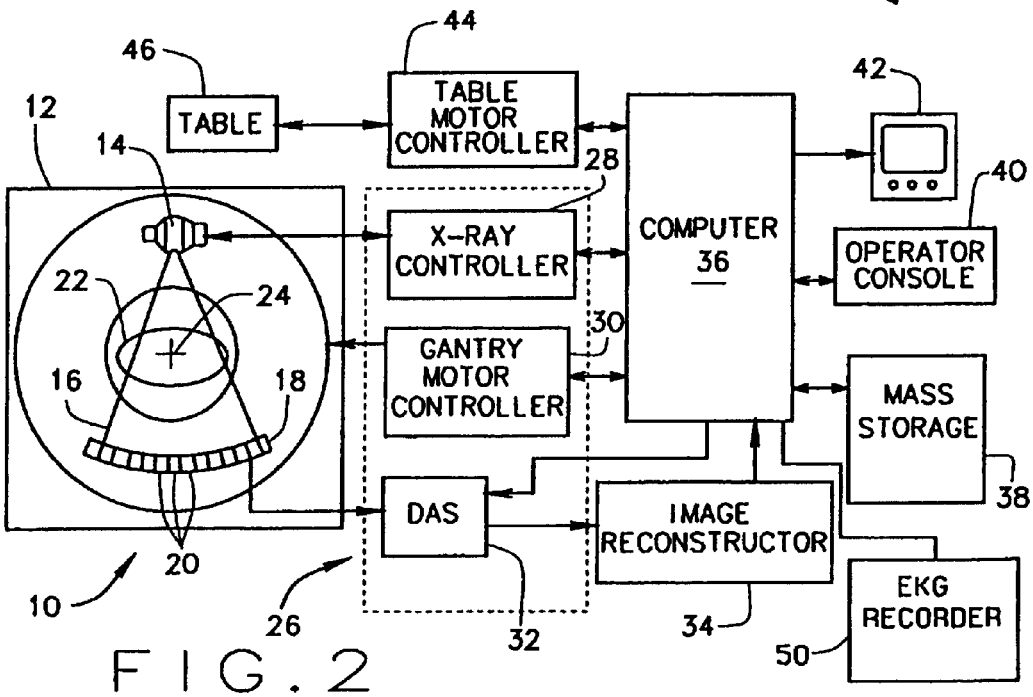
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameter from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particular, table 46 moves portions of patient 22 through gantry opening 48 along a z-axis. In some of the embodiments described below, cardiac cycles are measured utilizing EKG machine 50.

An amount of calcification present in the cardiac system of patient 22 is reliably estimated from scout images taken with CT imaging system 10 in one embodiment of the present invention. Patient 22 is instructed to hold his or her breath while images of the heart of patient 22 are scanned by CT imaging system 10 in a scout imaging mode of operation. Because patient 22 is holding his or her breath, the only moving object within the scan field of view is the heart of patient 22. Data for two scout scans are obtained, and a difference between the data for the two images is used to remove non-moving body structure and highlight calcification, as explained below.

Figure 3:
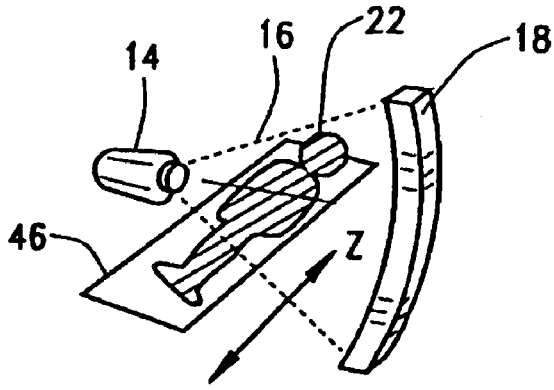
FIG. 3 is a representative of a portion of the system illustrated in FIG. 1 showing a patient translated by the table shown in FIG. 1 while the x-ray source and detector remain stationary during a scout scan.
Figure 4:
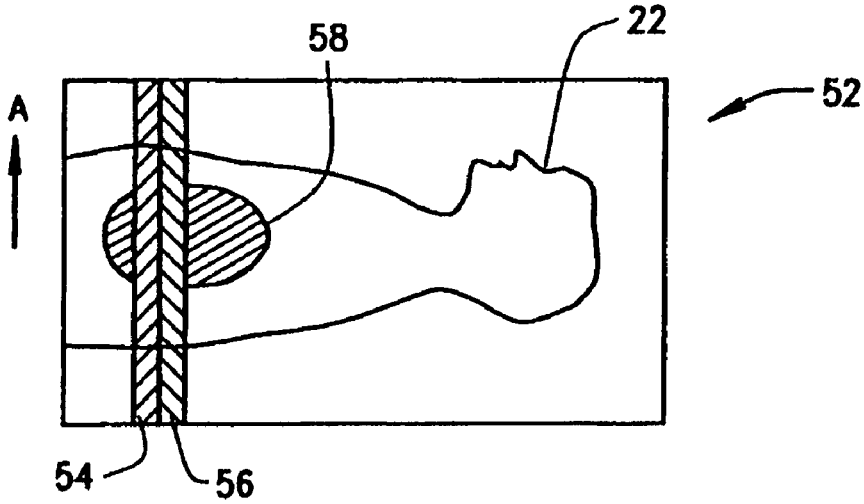
FIG. 4 is a representation of a scout image showing time relationships between columns of data that make up the scout image.

In one embodiment of the invention and referring to FIG. 3, scout-scanned data of patient 22 is acquired. Scout-scanned data is acquired by moving table 46 through gantry opening 48 in a z-direction while gantry 12 is held stationary. Thus, x-ray source 14 and detector array 18 are stationary, while data such as that represented in FIG. 4 is acquired. The acquired data represents a CT image of a region of the body of patient 22. Each column of scout image 52 is representative of x-ray attenuation data obtained at a certain instant of time. In one embodiment, each column of data, such as column 54 and column 56, is acquired in approximately 1 millisecond. Thus, each successive column of acquired data is sampled at a slightly different time. In FIG. 4, for example, column 54 is acquired at item t and at a displacement p from a starting position of the scout scan in a z-axis direction. Column 56, which is immediately adjacent to column 54, is acquired at time $t+\Delta t$, where $\Delta t$ is approximately 1 millisecond. Column 56 is located at displacement $p+\Delta p$ from the start of the scout scan. An entire scout scan image 52 sufficient for the present embodiment is taken in about two or three seconds. Data representing physical locations of a portion of the body of patient 22 including at least a portion of heart 58 is acquired and used for cardiac calcification scoring.

Data representing a second scout image (not shown) is also acquired. The second scout scan image is acquired in a manner that ensures that corresponding columns of the second scout scan are taken at times during which heart 58 is in a different phase of first scout image 52. In this manner, data representative of a first and a second scout-scanner CT image of physical locations of the body of patient 22 are obtained. Data for each physical location is obtained at different phases of the cardiac cycle in the two images.

Figure 5:
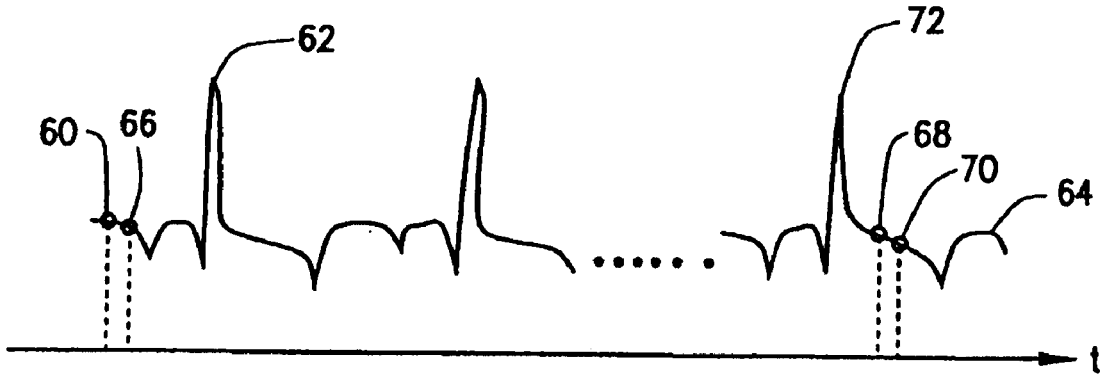
FIG. 5 is a simplified graphical representation of an electrocardiogram, showing times represented by columns in the scout image of FIG. 4 and a relationship between a first scout image and a second scout image in one embodiment of the present invention.

For example, referring to FIG. 5, column 54 of first scout image 52 is acquired at a time corresponding to phase 60 just prior to systole 62 of EKG signal 64. (EKG signal 64 is obtained by monitoring heart 58 of patient 22 using EKG machine 50.) Column 56 of scout image 52 is acquired at a time corresponding to phase 66. The second scout image is taken a few seconds after first scout image 52. By selection of a start time for its acquisition, corresponding columns of the second scout image are acquired at phases 68 and 70, immediately after systole 72. Both scout images are acquired at the same rate starting from the same position of patient 22 and table 46 moves at the same speed and in the same direction for each scout image acquisition in this embodiment. Thus, starting each scan at a different phase of EKG signal 64 is sufficient to ensure that corresponding columns in the two scans represent different phases of heart 58, assuming heart 58 is beating at a constant rate. This assumption is applicable because the entire procedure is completed in only a few seconds.

In one embodiment, scout scans are manually started. For example, phases of EKG signal 64 from EKG machine 50 are manually monitored to determine trigger times to begin each scout-scanned data acquisition. In another embodiment, scans are started automatically. For example, computer 36 of CT imaging system 10 is configured to receive and monitor EKG signal 64 or an equivalent to determine trigger times.

During scanning, patient 22 holds his or her breath and remains as still as possible to minimize differences between the first and the second scout images other than those related to heart movement. It is reasonable to request patients to hold their breath during the scanning and feasible for patients to comply with such requests due to the brevity of the procedure.

It will be observed that data for each scout image, for example, image 52, is a composite representing different phases of heart 58. Each physical location L represented by data of the first scout image is acquired at a phase $\phi_1(L)$ of the cardiac cycle. For the second scout image, data for location L is acquired at a phase $\phi_2(L)$, where $\phi_1(L)\neq\phi_2(L)$. Because of the amount of time taken by table 46 to travel from one end of each scout scan to the other, neither $\phi_1$ nor $\phi_2$ are constant across each scout image. However, their difference at any location L is constant, or nearly so. The present invention advantageously uses this difference to highlight cardiac calcification.

Figure 6:
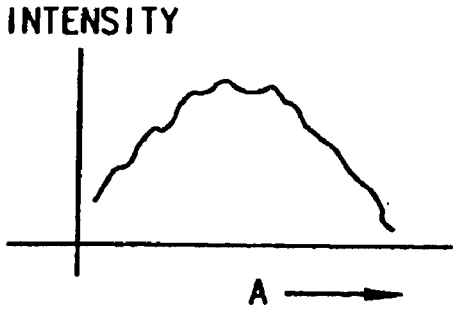
FIG. 6 is a simplified graphical representation of intensity vs. detector location in a column of a first scout scan.
Figure 7:
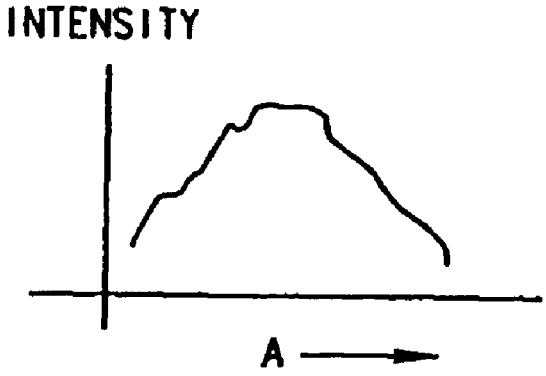
FIG. 7 is a simplified graphical representation of intensity vs. detector location in a column of a second scout scan corresponding to the column represented in FIG. 6.
Figure 8:
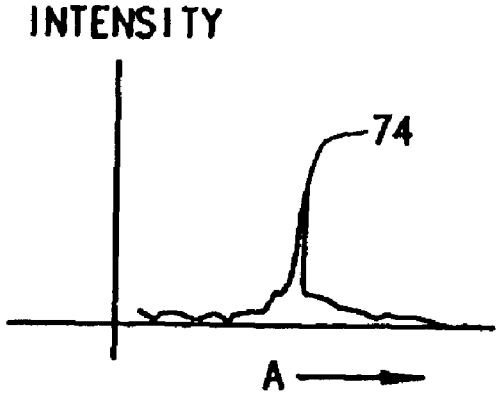
FIG. 8 is a representation of a difference between intensities as a function of detector location between data such as that represented in FIG. 6 and FIG. 7, whereby a calcium signal is isolated in one embodiment of the present invention.

Columns of intensity (or equivalently, attenuation) data is obtained by detector array 18 while table 46 moves to obtain a scout scan. Each column, for example column 54 shown in FIG. 4, represents data obtained simultaneously by different detector elements 20 of detector array 18. FIG. 6 represents a plot of intensity data received for a column in a first scout scan as a function of detector element position in the column. (Arrow A is shown in FIGS. 6, 7, and 8 to provide a directional reference with respect to FIG. 4. However, it should not be assumed that FIGS. 6, 7, and 8 are necessarily representative of the image shown in FIG. 4, nor should it be assumed that FIGS. 6, 7, and 8 are drawn to the same scale.) Although cardiac calcification data is present in FIG. 6, a calcification signal is not immediately evident. FIG. 7 shows a similar plot of a column in a second scout scan of patient 22 containing data representative of the same physical positions of patient 22, but at a different phase of the cardiac cycle of heart 58. An example of differences between two column signals such as those of FIG. 6 and FIG. 7 is plotted in FIG. 8. Because the body of patient 22 is essentially motionless except for beating heart 58 (disregarding motion of table 46), overlaying, non-moving body structures of patient 22 are removed by computing differences between the two scout images. As a result, the signals shown in FIG. 8 represent essentially only moving heart 58. Because calcification signals are stronger than those of soft tissue and because calcification deposits move with heart 58, signals from calcification deposits such as peak 74 are very apparent. Thus, when a difference image is determined between the two images that include the columns represented in FIGS. 6 and 7, peaks such as peak 74 are easily seen. Peak 74 is thus readily identified as a calcification deposit on a portions of the image corresponding to a moving body structures of patient 22. In one embodiment, computer 36 computes difference images and displays the computed difference images on CRT display 42. Calcification scoring is readily accomplished using these computed difference images, either manually using an image on CRT display 42 or automatically, using image processing techniques.

Figure 9:
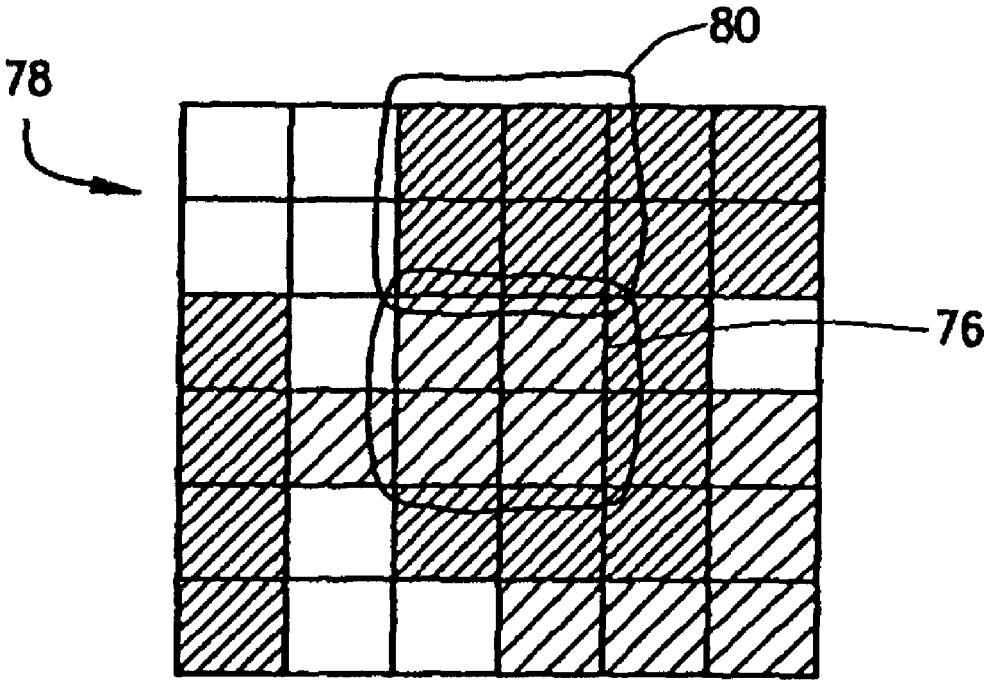
FIG. 9 is a representation of pixels of an image analyzed using image processing techniques in an embodiment of the present invention.

In one embodiment, image processing techniques are used by computer 36 to further isolate, identify, and score calcification peaks such as peak 74. For example, intensities of small groups of pixels 76 of a difference image 78 shown in part in FIG. 9 are compared to intensities of neighboring small groups of pixels 80, where a "small group of pixels" refers either to one pixel or a few pixels in a cluster. When a difference is determined to be greater than a predetermined threshold indicative of calcification, sites represented by pixels 76 are identified as calcification sites for further study. In one embodiment, results of the intensity comparison are used directly for scoring an amount of calcification in accordance with differences in image intensities. The scoring results are used as a guideline for further examination.

In one embodiment, a difference image is enhanced by image processing to enhance the appearance of calcification 74 utilizing, for example, contrast enhancement algorithms. Differencing or other image processing procedures needed for contrast enhancement are implemented, for example, in hardware, software, or firmware of image reconstructor 34 or computer 36, or both. In one embodiment, computer 36 is programmed both to display a difference image on CRT 42 and to automatically recognize and score calcification 74 by analysis of the difference image.

In one embodiment, scans of the two scout images are triggered by EKG signal 64 from EKG machine 50. The EKG signal is supplied to computer 36, which controls scanning and acquisition of image data in CT imaging system 10. Computer 36 ensures that the two scout images taken are images of the same region of the body of patient 22 by controlling movement of table 46. Computer 36 also ensures that the heart is in a different cardiac phase by staring the scans at different points in a cardiac cycle.

In an embodiment in which CT imaging system 10 is a multi-slice imaging system having more than one row of detector elements 20, similar procedures for movement of table 46 are followed. However, a plurality of difference images are obtained, one for each row of detector 18.

In another embodiment, multiple detector rows of a detector 16 in a multi-slice CT imaging system 10 are used in a single pass to generate a difference image. Computer 36 adjusts a rate of movement of table 46 during acquisition of data so that a small time lag occurs between acquisition of image data of the same body portions patient 22 by different rows of detector array 18. Computer 36 selects an amount of time lag in accordance with a heart rate of patient 22 determined, for example, from EKG signal 64. The amount of time lag is selected to ensure that image data is acquired by different rows of detector 18 during different portions of a cardiac cycle. In this manner, image data acquired from two different rows of a multi-slice detector 18 obtained during a single pass of a scout scan is used to obtain two suitable scout images. A difference image for scoring is computed from those portions of the two scout images that include at least a portion of heart 58 and that represent the same physical locations of the body of patient 22. Portions of each image acquired by the two rows of detector 18 that do not overlap are simply ignored.

In another embodiment utilizing a multi-slice CT imaging system 10 having more than two rows of detectors, additional information for estimating background noise in obtained. For example, three or more rows of detectors obtain three or more scout images, including two for computing a difference image, and noise estimation information including at least a third scout image. Background noise in the difference image is estimated and reduced utilizing the noise estimation information and standard signal processing techniques.

From the preceding description of various embodiments of the present invention, it is evident that the problem of motion-induced artifacts in CT imaging systems is overcome, especially for calcification scoring purposes. Moreover, by reducing or eliminating non-moving body parts in a difference image, scoring of calcification is readily accomplished, even though only small incremental x-ray attenuation is produced by calcification.

Although particular embodiments of the invention have been described and illustrated in detail, it is to be clearly understood that the same is intended by way of illustration and example only and is not to be taken by way of limitation. Accordingly, the spirit and scope of the invention are to be limited only by the terms of the appended claims and legal equivalents.

What is claimed is:

1. A method for producing CT images of a patient's heart suitable for calcification scoring, the heart having a cardiac cycle;

said method comprising the steps of:

acquiring data representative of a first scout-scanned CT image of physical locations of the patient's body including at least a portion of the patient's heart at phases $\phi_1(L)$ of the cardiac cycle;

acquiring data representative of a second scout-scanned CT image of the physical locations of the patient's body including at least a portion of the patient's heart at phases $\phi_2(L)$ of the cardiac cycle different from $\phi_1(L)$; and determining a difference image from the acquired data representative of the first scout-scanned CT image and the acquired data representative of the second scout-scanned CT image data[.] ;

*performing calcification scoring based on the difference image; and*

[producing] *outputting at least one of a calcification score and* CT images of the patient's heart based on the calcification scoring.

2. A method in accordance with claim 1 wherein the patient is holding his or her breath during both said image acquiring steps.

3. A method in accordance with claim 1 further comprising the step of identifying calcification deposits on portions of the difference image corresponding to moving body structures of the patient.

4. A method in accordance with claim 3 wherein said step of identifying calcification deposits is performed utilizing computer image processing.

5. A method in accordance with claim 3 wherein identifying calcification deposits on portions of the difference image corresponding to moving body structures of the patient comprises comparing intensities of neighboring pixel groups of the difference image to identify differences in intensity above a threshold indicative of calcification.

6. A method in accordance with claim 5 wherein identifying calcification deposits further comprises scoring an amount of calcification in accordance with differences in image intensities.

7. A method in accordance with claim 1 further comprising the step of processing the difference image to enhance appearance of calcification deposits.

8. A method in accordance with claim 1 further comprising the step of monitoring an EKG signal of the patient's heart to determine trigger times for acquiring the data representative of the first image and the data representative of the second image at different phases of the cardiac cycle.

9. A method in accordance with claim 1 wherein both steps of acquiring data are performed [at the same time] *by* utilizing different detector rows of a multi-slice CT imaging system.

10. A method in accordance with claim 9 wherein the CT imaging system comprises a table configured to move the patient during a scout scan, and further comprising the step of adjusting a rate at which the table moves during said data acquiring steps in accordance with a heart rate of the patient.

11. A method in accordance with claim 10 wherein the multi-slice CT imaging system comprises at least three detector rows, and said method further comprises the steps of acquiring noise estimation information including data representative of a third scout-scanned image, and estimating background noise in the difference image utilizing the noise estimation information.

12. A CT imaging system for obtaining images of a patient's heart suitable for calcification scoring, the heart having a cardiac cycle;

said system configured to:

acquire data representative of a first scout-scanned CT image of physical locations of the patient's body including at least a portion of the patient's heart at phases $\phi_1(L)$ of the cardiac cycle;

acquire data representative of a second scout-scanned CT image of the physical locations of the patient's body including at least a portion of the patient's heart at phases $\phi_2(L)$ of the cardiac cycle different from $\phi_1(L)$; and determine a difference image from the acquired data representative of the first scout-scanned CT image and the acquired data representative of the second scout scanned CT image data.

13. A system in accordance with claim 12 further configured to identify calcification deposits on portions of the difference image corresponding to moving body structures of the patient.

14. A system in accordance with claim 13 configured to identify calcification deposits utilizing computer image processing.

15. A system in accordance with claim 13 wherein said system being configured to identify calcification deposits on portions of the difference image corresponding to moving body structures of the patient comprises said system being configured to compare intensities of neighboring pixel groups of the difference image to identify differences in intensity above a threshold indicative of calcification.

16. A system in accordance with claim 15 wherein said system being configured to identify calcification deposits further comprises said system being configured to score an amount of calcification in accordance with differences in image intensities.

17. A system in accordance with claim 12 further configured to process the difference image to enhance appearance of calcification deposits.

18. A system in accordance with claim 12 further configured to monitor an EKG signal of the patient's heart to determine trigger times for acquiring the data representative of the first image and the data representative of the second image at different phases of the cardiac cycle.

19. A system in accordance with claim 12 having a multi-scale detector, said system being configured to acquire both the data representative of the first image and the data representative of the second image [at the same time] *by* utilizing different detector rows of said multi-slice detector.

20. A system in accordance with claim 19 further comprising a table configured to move the patient during a scout scan, and further configured to adjust a rate at which the table moves during scout-scanned data acquisition in accordance with a heart rate of the patient.

21. A system in accordance with claim 20 wherein said multi-slice detector comprises at least three detector rows, and said system is further configured to acquire noise estimation information including data representative of a third scout-scanned image, and to estimate background noise in the difference image utilizing the noise estimation information.

*22. A method for facilitating calcification scoring, said method comprising:*

*imaging a heart at a first phase of a cardiac cycle to obtain a first image;*

*imaging the heart at a second phase of the cardiac cycle to obtain a second image, wherein the second phase is different from the first phase, and wherein the first and second images are obtained at the same physical location in a single scan;*

*determining a difference image using the first and second images;*

*identifying calcification deposits on portions of the difference image that correspond to moving body structures of the patient; and*

*performing calcification scoring based on the difference image.*

*23. A method in accordance with claim 22 further comprising instructing the patient to hold his or her breath during imaging.*

*24. A method in accordance with claim 22 wherein the calcification deposits are identified utilizing computer image processing.*

*25. A method in accordance with claim 22 wherein identifying calcification deposits on portions of the difference image that correspond to moving body structures of the patient comprises comparing intensities of neighboring pixel groups of the difference image to identify differences in intensity above a threshold indicative of calcification.*

*26. A method in accordance with claim 25 wherein identifying calcification deposits further comprises scoring an amount of calcification in accordance with differences in image intensities.*

*27. A method in accordance with claim 22 further comprising processing the difference image to enhance appearance of calcification deposits.*

*28. A method in accordance with claim 22 further comprising:*

*monitoring an EKG signal of the patient's heart to determine trigger times for imaging the heart to obtain a first image; and*

*imaging the heart to obtain a second image at different phases of the cardiac cycle.*

*29. A method in accordance with claim 22 wherein imaging the heart to obtain a first image and imaging the heart to obtain a second image are performed by utilizing different detector rows of an imaging system.*

*30. A method in accordance with claim 29 wherein the imaging system includes a table configured to move the patient during imaging, said method further comprises adjusting a rate at which the table moves during imaging in accordance with the cardiac cycle of the patient.*

*31. A method in accordance with claim 30 wherein the imaging system includes at least three detector rows, said method further comprises:*

*acquiring noise estimation information including data representative of a third image; and*

*estimating background noise in the difference image utilizing the noise estimation information.*

* * * * *